United States Patent [19]

Stetter et al.

[11] Patent Number: 4,693,979
[45] Date of Patent: Sep. 15, 1987

[54] TYPE II RESTRICTION ENDONUCLEASE MAE II, A PROCESS FOR OBTAINING IT AND THE USE THEREOF

[75] Inventors: Karl O. Stetter, Regensburg; Rüdiger Schmitt, Niedergebraching/Pentling, both of Fed. Rep. of Germany

[73] Assignee: Boehringer Mannheim GmbH, Mannheim-Waldhof, Fed. Rep. of Germany

[21] Appl. No.: 655,469

[22] Filed: Sep. 28, 1984

[30] Foreign Application Priority Data

Jan. 18, 1984 [DE] Fed. Rep. of Germany ....... 3401619

[51] Int. Cl.$^4$ .......................... C12N 9/22; C12N 9/16; C12N 15/00; C12R 1/01
[52] U.S. Cl. .................................. 435/199; 435/196; 435/172.3; 435/822
[58] Field of Search ............... 435/195, 196, 199, 822, 435/91, 172.3

[56] References Cited
PUBLICATIONS

Schmid, K. et al, *Nuc. Acids Res.*, vol. 12, No. 6, pp. 2619-2628, Mar. 1984.
Balch, W. et al, *Micro Revs.*, vol. 43, No. 2, pp. 260-264, 285 and 286, 1979.

*Primary Examiner*—Thomas G. Wiseman
*Assistant Examiner*—Jayme A. Huleatt
*Attorney, Agent, or Firm*—Felfe & Lynch

[57] ABSTRACT

The present invention provides a restriction endonuclease, characterized by the palindromic recognition sequence:

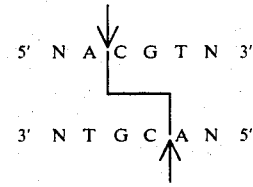

and the cleavage position defined by the arrows.

The present invention also provides a process for obtaining the new restriction endonuclease.

6 Claims, No Drawings

TYPE II RESTRICTION ENDONUCLEASE MAE II, A PROCESS FOR OBTAINING IT AND THE USE THEREOF

The present invention is concerned with the new Type II restriction endonuclease MaeII, with a process for obtaining it and with the use thereof.

Type II restriction endonucleases are endodeoxyribonucleases which are able to recognize and cleave certain DNA at nucleotide sequences. Phosphodiester bridges are thereby hydrolysed in the target sequence, namely one in each polynucleotide strand. Therefore, Type II restriction endonucleases are valuable for the analysis of DNA molecules.

Specific Type II restriction endonucleases are admittedly already known for numerous recognition sequences, but there is still a need for the provision of further Type II restriction endonucleases which are specific for such recognition sequences for which restriction endonucleases have not been recognized.

Therefore, it is an object of the present invention to provide a new restriction endonuclease which is able specifically to recognize and cleave a sequence hitherto not recognized by any such enzyme.

Thus, according to the present invention, there is provided a restriction endonuclease which is characterized by the palindromic recognition sequence

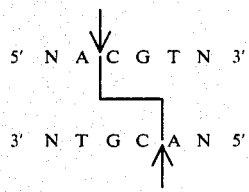

and the cleavage position defined by the arrow.

The new Type II restriction endonuclease according to the present invention, which in the following is called MaeII, has a temperature optimum between 45° and 48° C. and a pH optimum at 8.0/45° C. in Tris/HCl buffer. Further optimum reaction parameters are 175 mM sodium chloride, 2 to 6 mM $Mg^{2+}$ and 2 to 8 mM 2-mercaptoethanol. The presence of magnesium ions is essential for the activity.

As mentioned above, the enzyme acts on palindromic stuctures and thus recognizes a self-complementary structure in which the complementary strand of the DNA displays the identical sequence in the opposite-running direction.

The recognition sequence and the point of cleavage of the enzyme can be ascertained as follows: he plasmid pBR322 is completely digested with HinfI. The HinfI fragments B and C (517 bp and 506 bp, respectively) are isolated, their 3'-ends are marked with alpha-[$^{32}$P] dATP and Klenow polymerase and subsequently cleaved with AluI. From the marked fragments which hereby result, there is isolated and sequenced the 475 bp fragment (pBR322, position 1526 to 2000, length of the fragment including single strand ends).

An aliquot of the 475 bp fragment is cleaved with the enzyme according to the present invention resulting in three fragments. The cleavage position 1546 lying next to the 3'labeled end was determined.

The length of the HinfI/MaeII fragment is determined in sequence gels. The HinfI/MaeII fragment thereby runs in the gel like the "A" of the sequence ladder in the recognition sequence

5'-ACGT-3'.

Therefore, it terminates with the nucleotide C of the recognition sequence. Thus, the cleavage position of the MaeII is between nucleotide A and C.

According to the present invention, MaeII is obtained by culturing *Methanococcus aeolicus* DSM 2835 and the enzyme is recovered from the cells. For the recovery, there can be used conventional biochemical purification methods, the presence of the enzyme in the particular fractions obtained thereby being easily detectable on the basis of the cleavage of its recognition sequence. As substrate there can be used, for example, pBR322-DNA. The DNA fragments obtained are electrophoretically separated in agarose gels in the buffer systems conventional for fragment separation in the presence of ethidium bromide.

The microorganism used for obtaining the enzyme grows anaerobically in Medium III (Microbiol. Reviews, 43, 260–296/1979) on $H_2/CO_2$ or on formate. It forms regular to irregular cocci of about 2 μm diameter, individually or in pairs. On agar, there are formed round, convex, pale ochre-coloured colonies of about 2 mm diameter. The microorganism is gram negative. The cell integument consists of protein subunits. Growth takes place at a temperature of 25° to 50° C., the temperature optimum being 45° C. (2 hour duplication time). Growth takes place in the presence of 1.5 to 5% and optimally of 4% sodium chloride. The DNA base composition is about 28.6% G+C. Therefore, the microorganism differs from the known Methanococci by a somewhat lower GC content of the DNA, by the optimum growth temperature of 45° C., by the markedly larger cells and by the presence of new restriction enzymes. Methanococcus aeolicus has been deposited at the Deutsches Sammlung von Mikroorganismen, Gesellschaft für Biotechnologische Forschung GmbH, Grisebachstrasse 8, 3400 Göttingen, Federal Republic of Germany, and bears Accession Number DSM 2835.

In a preferred embodiment of the process according to the present invention, the cells are digested the extract is mixed with polyethyleneimine up to a concentration of 0.65%, the precipitate is separated off and from the supernatant there is obtained the fraction precipitating up to 95% ammonium sulphate saturation.

For the digestion, there can be used the conventional mechanical and chemical methods, for example, high pressure dispersion, ultrasonics or enzymatic digestion.

Further purification of the ammonium sulphate fraction containing the new enzyme is preferably conducted by molecular sieve fractionation, chromatography on anion exchangers and on cation exchangers, as well as subsequent affinity chromatography. As molecular sieve material, there has proved useful the product commercially available under the trade name Ultrogel AcA 34, this being an acrylamide/agarose heteropolymer of 3% acrylamide and 4% agarose. As anion exchangers, there can be used carrier materials based on sepharose, cellulose or synthetic polymers modified with diethylaminoethyl substituents, for example the product of Pharmacia, Uppsala, Sweden, available under the trade name DEAE-Sephacel.

As cation exchangers, there are preferred phosphate group-containing substances, preferably carbohydrates, for example cellulose phosphate and the like. For the affinity chromatography, carrierfixed heparin, for example heparin-sepharose, has proved to be especially useful.

The following examples are given for the purpose of illustrating the present invention:

EXAMPLE 1

*Methanococcus aeolicus* DSM 2835 is allowed to grow anaerobically in minimal fromate medium, which is described in detail hereinafter, at 45° C. for 3 days and then harvested in the stationary phase. 35 g of the so obtained cell paste are suspended in 70 ml digestion buffer (40 mM Tris/HCl, pH 8.0/4° C.; 0.1 mM EDTA (ethylenediamine-tetraacetic acid); 7 mM 2-mercaptoethanol and 0.2 mM PMSF (phenylmethanesulphonyl fluoride). The cells are then digested twice by high pressure dispersion in a pre-cooled pressure cell at 1100 bar ≘16,000 PSI.

To the digestion suspension ammonium chloride is added to a final concentration of 0.3M. Subsequently, 7 ml of 10% polyethyleneimine solution are added up to a final concentration of 0.65% v/v. After leaving to stand for 30 minutes at 4° C., the precipitate formed is centrifuged off for 60 minutes at 27,300 g or 23,000 g and discarded. The supernatant is mixed with solid ammonium sulphate up to 95% saturation. After 16 hours at 4° C., the ammonium sulphate precipitate is centrifuged off for 60 minutes at 27,300 g or 23,000 g.

The minimal medium has the following composition:

| dissolve: | g/litre |
|---|---|
| KCl | 0.32 g |
| MgCl$_2$.6H$_2$O | 2.75 g |
| MgSO$_4$.7H$_2$O | 3.45 g |
| NH$_4$Cl | 0.25 g |
| CaCl$_2$.2H$_2$O | 0.15 g |
| K$_2$HPO$_4$ | 0.15 g |
| NaCl | 18 g |
| mineral elixir (see below) | 10 ml |
| Fe(NH$_4$)$_2$(SO$_4$)$_2$.7H$_2$O | 2 mg |
| NaHCO$_3$ (add at end) | 5.5 g |
| resazurin 0.1% | 1 ml |
| sodium formate | 15 g |
| sodium tungstate | 3.3 mg |

| add 50 ml reducing agent consisting of: | |
|---|---|
| Na$_2$S | 12.5 g/litre allow nitrogen to bubble through |
| fresh 1 N NaOH | 75 ml |
| resazurin 0.1% | 1 ml | adjust the pH value to 6.9 with formic acid and make up to 1 liter, allow nitrogen to bubble through.

| Mineral elixir | g/litre |
|---|---|
| Titriplex I | 1.5 g |
| MgSO$_4$.7H$_2$O | 3.0 g |
| MnSO$_4$.2H$_2$O | 0.5 g |
| NaCl | 1.0 g |
| FeSO$_4$.7H$_2$O | 0.1 g |
| CoSO$_4$ or CoCl$_2$ | 0.1 g |
| CaCl$_2$.2H$_2$O | 0.1 g |
| ZnSO$_4$ | 0.1 g |
| CuSO$_4$.5H$_2$O | 0.01 g |
| KAl(SO$_4$)$_2$ | 0.01 g |
| H$_3$BO$_3$ | 0.01 g |

| Mineral elixir | g/litre |
|---|---|
| Na$_2$MoO$_4$.2H$_2$O | 0.01 g slowly adjust pH value to 6.5 with 5 N KOH |

EXAMPLE 2

The ammonium sulphate precipitate obtained according to example 1 is taken up with TEMG buffer (40 mM Tris/HCl, pH 8.0/4° C.; 0.1 mM EDTA, 7 mM 2-mercaptoethanol; 10% v/v glycerol) and 0.5M NaCl and applied to an Ultrogel AcA-34 molecular sieve column of 3×100 cm. This column is eluted with TEMG buffer+0.5M NaCl and the eluate fractions with MaeII activity are combined.

The combined eluate fractions are chromatographed on an anion exchanger column (DEAE-Sephacel; 2×10 cm) equilibrated with TEMG buffer. After washing with 2 column volumes of TEMG buffer, the enzyme is eluted with a linear gradient 0 to 1M NaCl in TEMG. The enzyme appears in the fractions with 0.15 to 0.35M NaCl. The active fractions are combined and dialysed against TEMG buffer. The dialysate is chromatographed on a cation exchanger column (cellulose phosphate P 11; 1×10 cm) equilibrated with TEMG buffer. Washing and elution take place as in the case of the anion exchanger column. MaeII as eluted between 0.3 and 0.5M NaCl. The combined, enzyme-containing fractions are again dialysed against TEMG buffer and the dialysate chromatographed on an affinity chromatography column (heparin-sepharose CL-6B; 1×5 cm) equilibrated with TEMG buffer. Washing and elution again take place as described in the case of the anion exchanger column. MaeII is eluted between 0.4 and 0.6M NaCl. The active fractions are combined and dialysed against 20 mM Tris/HCl buffer, pH 8.0/4° C., containing 0.1 mM EDTA, 10 mM 2-mercaptoethanol, 100 mM NaCl, 50 vol.% glycerol, 0.01 vol.% Triton X100, and stored at −20° C. The activity is about 300 U MaeII (activity definition: 1U=1 μg pBR322-DNA/hour at 45° C. completely cleaved).

DETERMINATION OF ACTIVITY

Into a mixture of 5 μl incubation buffer containing 0.03M Tris/HCl, pH 8.0/45° C., 0.875M NaCl, 0,03M MgCl$_2$, 0.035M 2-mercaptoethanol and 0.05 vol.% Triton X100 are introduced 14 μl water and 5 μl pBR322-DNA (4 OD/ml), as well as 1 μl MaeII solution (1U/μl). The solution is kept at 45° C. for 1 hour, cooled on ice and mixed with 5 μl cold stop solution, contained 7M urea, 20% w/v sucrose, 0,06M EDTA and 0.01% w/v bromophenol blue. It is then separated electrophoretically on 1% agarose gel for 3 to 4 hours at 100 V. The bands obtained are identified in comparison with suitable DNA length standards.

We claim:

1. A restriction endonuclease which capable of recognizing and cleaving a DNA sequence at a position indicated by the arrows

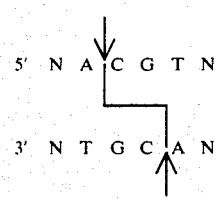

2. The restriction endonuclease of claim 1 wherein said endonuclease is characterized by a temperature optimum between 45° and 48° C. and a pH optimum at 8.0/45° C. in Tris HCl buffer.

3. A process for obtaining the restriction endonuclease of claim 1 comprising the steps of culturing *Methanococcus aeolicus* DSM 2835 cells and recovering the restriction endonuclease from the cells.

4. The process of claim 3 comprising recovering the endonuclease from the cells of *Methanococcus aeolicus* by digesting the cells to release an extract therefrom, mixing the extract released from the digested cells with polyethylenimine up to a concentration of 0.65% v/v, separating off insolubles and leaving a supernatant, mixing the supernatant with ammonium sulphate in an amount of up to 95% saturation to form a precipitated fraction and recovering the precipitated fraction.

5. The process of claim 4, further comprising purifying the ammonium sulphate precipitated fraction by at least one process selected from the group consisting of molecular sieve fractionation, chromatography over a weakly basic anion exchanger, chromatography over a weakly acidic cation exchanger, and affinity chromatography.

6. The process of claim 5, wherein carrier-fixed heparin is used for the affinity chromatography.

* * * * *